(12) United States Patent
Bergeron et al.

(10) Patent No.: US 9,446,024 B2
(45) Date of Patent: Sep. 20, 2016

(54) FORMULATIONS FOR THE TREATMENT OF VAGINAL DISORDERS

(71) Applicants: Mission Pharmacal Company, San Antonio, TX (US); Universite Laval, Quebec (CA)

(72) Inventors: Michel G. Bergeron, Quebec (CA); Jian Gao, San Antonio, TX (US); Rabeea F. Omar, Quebec (CA); Mary Ann Walter, San Antonio, TX (US)

(73) Assignees: Université Laval, Quebec (CA); Mission Pharmacal Company, San Antonio, TX (US)

( * ) Notice: Subject to any disclaimer, the term of this patent is extended or adjusted under 35 U.S.C. 154(b) by 0 days.

(21) Appl. No.: 14/314,759

(22) Filed: Jun. 25, 2014

(65) Prior Publication Data

US 2015/0080443 A1  Mar. 19, 2015

Related U.S. Application Data

(60) Provisional application No. 61/839,070, filed on Jun. 25, 2013.

(51) Int. Cl.

| *A61K 31/415* | (2006.01) |
| *A61K 31/4164* | (2006.01) |
| *A61K 9/00* | (2006.01) |
| *A61K 47/10* | (2006.01) |
| *A61K 9/06* | (2006.01) |
| *A61K 47/22* | (2006.01) |

(52) U.S. Cl.
CPC .......... *A61K 31/4164* (2013.01); *A61K 9/0034* (2013.01); *A61K 9/06* (2013.01); *A61K 47/10* (2013.01); *A61K 47/22* (2013.01)

(58) Field of Classification Search
USPC ........................................... 514/386
See application file for complete search history.

(56) References Cited

U.S. PATENT DOCUMENTS

| 4,837,378 A | 6/1989 | Borgman |
| 5,536,743 A | 7/1996 | Borgman |
| 5,840,744 A | 11/1998 | Borgman |
| 6,068,851 A | 5/2000 | Bergeron et al. |
| 6,348,203 B1 | 2/2002 | Goodman et al. |
| 6,423,307 B2 | 7/2002 | Saettone et al. |
| 6,500,460 B1 | 12/2002 | Bergeron et al. |
| 7,192,607 B2 | 3/2007 | Bergeron et al. |
| 7,456,207 B2 | 11/2008 | Bentley et al. |
| 7,465,295 B2 | 12/2008 | Bergeron et al. |
| 7,893,097 B2 | 2/2011 | Yang et al. |
| 8,349,368 B2 | 1/2013 | Gordon et al. |
| 2006/0093675 A1* | 5/2006 | Ebmeier ............. A61K 9/0034 424/487 |
| 2007/0224226 A1 | 9/2007 | Levinson et al. |
| 2007/0231358 A1 | 10/2007 | Ebmeier et al. |
| 2008/0242731 A1* | 10/2008 | Vancaillie ............ A61K 31/164 514/626 |
| 2009/0030060 A1 | 1/2009 | Ebmeier et al. |
| 2010/0105750 A1 | 4/2010 | Aksamit et al. |
| 2011/0082179 A1 | 4/2011 | Yang et al. |
| 2013/0005787 A1 | 1/2013 | Nordsiek et al. |

FOREIGN PATENT DOCUMENTS

| EP | 0 357 787 B1 | | 5/1996 |
| WO | WO 88/06888 | | 9/1988 |
| WO | WO 90/14832 | | 12/1990 |
| WO | WO 2005/087270 | * | 9/2005 |
| WO | WO 2005/087270 A1 | | 9/2005 |
| WO | WO 2006/050303 A2 | | 5/2006 |

OTHER PUBLICATIONS

Schwebke et. al. (Am. J. Obstet. Gynecol. (2011) 204:211.e1-211e6).*
Saurina et. al. (Clinical Infectious Diseases (1998) 26:1238-1239).*
Ruzin (Plant Microtechnique and Microscopy (1999).*

* cited by examiner

*Primary Examiner* — Marcos Sznaidman
(74) *Attorney, Agent, or Firm* — Sterne, Kessler, Goldstein & Fox P.L.L.C.

(57) ABSTRACT

The present disclosure provides novel formulations suitable for the intravaginal delivery of tinidazole, as well as methods of using the same.

3 Claims, 17 Drawing Sheets

Figure 1

| Observations | Numerical Grading |
|---|---|
| Erythema | |
| No Redness | 0 |
| Slight Redness | 1 |
| Redness with Distinct blood vessels | 2 |
| Deep redness accompanied with numerous engorged blood vessels | 3 |
| Exudate | |
| No pus | 0 |
| Few small globules of pus | 1 |
| Large globules of pus | 2 |
| Large amounts of pus and or sloughed tissue exuding from the vulva | 3 |
| Edema | |
| No swelling of the vulva | 0 |
| Slight swelling of the vulva to less than twice its size | 1 |
| Swelling of the vulva to twice its size | 2 |
| Swelling of the vulva to greater than twice its size | 3 |

Figure 2

| Animal # | Group | Day 0 | | | Day 1 | | | Day 2 | | | Day 3 | | | Day 4 | | | Day 5 | | | Total | Irritation Score | CII |
|---|---|---|---|---|---|---|---|---|---|---|---|---|---|---|---|---|---|---|---|---|---|---|
| | | ER | EX | ED | ER | EX | ED | ER | EX | ED | ER | EX | ED | ER | EX | ED | ER | EX | ED | | | |
| 30428 | Test | 1 | 0 | 0 | 1 | 0 | 1 | 2 | 0 | 1 | 2 | 0 | 1 | 2 | 0 | 1 | 2 | 0 | 1 | 14 | 0.9 | |
| 30439 | Test | 1 | 0 | 0 | 2 | 0 | 1 | 2 | 0 | 1 | 2 | 0 | 1 | 2 | 0 | 1 | 2 | 0 | 1 | 15 | 1.0 | 1.0 |
| 30440 | Test | 1 | 0 | 0 | 2 | 0 | 1 | 2 | 0 | 1 | 2 | 0 | 1 | 2 | 0 | 1 | 2 | 0 | 1 | 15 | 1.0 | |
| 30424 | Control | 1 | 0 | 0 | 2 | 0 | 1 | 2 | 0 | 1 | 1 | 0 | 1 | 1 | 0 | 1 | 2 | 0 | 1 | 13 | 0.9 | |
| 30425 | Control | 0 | 0 | 1 | 1 | 0 | 1 | 1 | 0 | 1 | 1 | 0 | 1 | 1 | 0 | 1 | 1 | 0 | 2 | 11 | 0.7 | 0.9 |
| 30426 | Control | 0 | 0 | 0 | 2 | 0 | 1 | 2 | 0 | 1 | 2 | 0 | 1 | 2 | 0 | 1 | 2 | 0 | 2 | 16 | 1.1 | |
| | | | | | | | | | | | | | | | | | Difference (test − control) | | | | 0.1 | |

ER = erythema
EX = exudate
ED = edema
CII = Cumulative Irritation Index

Figure 3

| Animal # | Group | Day 0 | | | Day 1 | | | Day 2 | | | Day 3 | | | Day 4 | | | Day 5 | | | Total | Irritation Score | CII |
|---|---|---|---|---|---|---|---|---|---|---|---|---|---|---|---|---|---|---|---|---|---|---|
| | | ER | EX | ED | ER | EX | ED | ER | EX | ED | ER | EX | ED | ER | EX | ED | ER | EX | ED | | | |
| 30231 | Test | 1 | 0 | 0 | 1 | 0 | 0 | 1 | 0 | 0 | 1 | 0 | 0 | 1 | 0 | 0 | 1 | 0 | 1 | 6 | 0.4 | |
| 30233 | Test | 1 | 0 | 0 | 1 | 0 | 0 | 1 | 0 | 0 | 1 | 0 | 0 | 2 | 0 | 0 | 2 | 0 | 0 | 7 | 0.5 | 0.6 |
| 30251 | Test | 1 | 0 | 0 | 2 | 0 | 1 | 2 | 0 | 1 | 1 | 0 | 1 | 2 | 0 | 1 | 2 | 0 | 1 | 14 | 0.9 | |
| 30427 | Control | 1 | 0 | 0 | 1 | 0 | 0 | 1 | 0 | 0 | 1 | 0 | 0 | 1 | 0 | 0 | 1 | 0 | 0 | 6 | 0.4 | |
| 30086 | Control | 1 | 0 | 0 | 1 | 0 | 0 | 1 | 0 | 0 | 1 | 0 | 0 | 1 | 0 | 0 | 3 | 0 | 1 | 8 | 0.5 | 0.4 |
| 30093 | Control | 1 | 0 | 0 | 1 | 0 | 0 | 1 | 0 | 0 | 1 | 0 | 0 | 1 | 0 | 0 | 1 | 0 | 1 | 6 | 0.4 | |
| | | | | | | | | | | | | | | | | | Difference (test − control) | | | | 0.2 | |

ER = erythema
EX = exudate
ED = edema
CII = Cumulative Irritation Index

Figure 4

| Animal # | Group | Day 0 | | | Day 1 | | | Day 2 | | | Day 3 | | | Day 4 | | | Day 5 | | | Total | Irritation Score | CII |
|---|---|---|---|---|---|---|---|---|---|---|---|---|---|---|---|---|---|---|---|---|---|---|
| | | ER | EX | ED | ER | EX | ED | ER | EX | ED | ER | EX | ED | ER | EX | ED | ER | EX | ED | | | |
| 30535 | Test | 1 | 0 | 0 | 2 | 0 | 1 | 2 | 0 | 1 | 2 | 0 | 2 | 2 | 0 | 1 | 2 | 1 | 2 | 18 | 1.2 | |
| 30536 | Test | 0 | 0 | 0 | 1 | 0 | 0 | 1 | 0 | 0 | 1 | 0 | 0 | 1 | 0 | 0 | 0 | 0 | 0 | 4 | 0.3 | 0.6 |
| 30537 | Test | 1 | 0 | 0 | 1 | 0 | 0 | 1 | 0 | 0 | 1 | 0 | 0 | 1 | 0 | 0 | 1 | 0 | 0 | 5 | 0.3 | |
| 30545 | Control | 1 | 0 | 0 | 0 | 0 | 0 | 0 | 0 | 0 | 0 | 0 | 0 | 0 | 0 | 0 | 0 | 0 | 0 | 1 | 0.1 | |
| 30544 | Control | 1 | 0 | 0 | 1 | 0 | 0 | 1 | 0 | 0 | 1 | 0 | 0 | 1 | 0 | 0 | 1 | 0 | 0 | 5 | 0.3 | 0.3 |
| 30539 | Control | 1 | 0 | 0 | 1 | 0 | 0 | 1 | 0 | 0 | 1 | 0 | 1 | 1 | 0 | 1 | 1 | 1 | 1 | 9 | 0.6 | |
| | | | | | | | | | | | | | | | | | Difference (test – control) | | | | 0.3 | |

ER = erythema
EX = exudate
ED = edema
CII = Cumulative Irritation Index

Figure 5

| Animal # | Group | Day 0 | | | Day 1 | | | Day 2 | | | Day 3 | | | Day 4 | | | Day 5 | | | Total | Irritation Score | CII |
|---|---|---|---|---|---|---|---|---|---|---|---|---|---|---|---|---|---|---|---|---|---|---|
| | | ER | EX | ED | ER | EX | ED | ER | EX | ED | ER | EX | ED | ER | EX | ED | ER | EX | ED | | | |
| 30565 | Test | 0 | 0 | 0 | 0 | 0 | 0 | 1 | 0 | 0 | 1 | 0 | 0 | 1 | 0 | 0 | 1 | 0 | 0 | 4 | 0.3 | |
| 30564 | Test | 1 | 0 | 0 | 1 | 0 | 1 | 1 | 0 | 0 | 1 | 0 | 1 | 1 | 0 | 1 | 1 | 0 | 1 | 9 | 0.6 | 0.5 |
| 30568 | Test | 0 | 0 | 0 | 1 | 0 | 0 | 1 | 0 | 1 | 1 | 0 | 1 | 1 | 0 | 1 | 1 | 0 | 1 | 9 | 0.6 | |
| 30559 | Control | 0 | 0 | 0 | 0 | 0 | 0 | 1 | 0 | 0 | 1 | 0 | 0 | 0 | 0 | 0 | 1 | 0 | 0 | 3 | 0.2 | |
| 30561 | Control | 0 | 0 | 0 | 0 | 0 | 0 | 1 | 0 | 1 | 1 | 0 | 0 | 1 | 0 | 0 | 1 | 0 | 1 | 6 | 0.4 | 0.4 |
| 30562 | Control | 1 | 0 | 0 | 1 | 0 | 0 | 1 | 0 | 1 | 1 | 0 | 1 | 1 | 0 | 1 | 2 | 0 | 2 | 11 | 0.7 | |
| | | | | | | | | | | | | | | | | | Difference (test − control) | | | | 0.1 | |

ER = erythema
EX = exudate
ED = edema
CII = Cumulative Irritation Index

Figure 6

| Animal # | Group | Day 0 | | | Day 1 | | | Day 2 | | | Day 3 | | | Day 4 | | | Day 5 | | | Total | Irritation Score | CII |
|---|---|---|---|---|---|---|---|---|---|---|---|---|---|---|---|---|---|---|---|---|---|---|
| | | ER | EX | ED | ER | EX | ED | ER | EX | ED | ER | EX | ED | ER | EX | ED | ER | EX | ED | | | |
| 30555 | Test | 1 | 0 | 0 | 1 | 0 | 0 | 2 | 0 | 0 | 1 | 0 | 0 | 1 | 0 | 0 | 1 | 0 | 0 | 6 | 0.4 | |
| 30557 | Test | 0 | 0 | 0 | 0 | 0 | 0 | 2 | 0 | 0 | 3 | 0 | 3 | 3 | 0 | 3 | 2 | 0 | 2 | 18 | 1.2 | 0.6 |
| 30556 | Test | 0 | 0 | 0 | 0 | 0 | 0 | 1 | 0 | 0 | 1 | 0 | 0 | 1 | 0 | 0 | 1 | 0 | 1 | 5 | 0.3 | |
| 30550 | Control | 0 | 0 | 0 | 0 | 0 | 0 | 0 | 0 | 0 | 1 | 0 | 0 | 1 | 0 | 0 | 1 | 0 | 0 | 3 | 0.2 | |
| 30553 | Control | 1 | 0 | 0 | 1 | 0 | 0 | 1 | 0 | 0 | 1 | 0 | 0 | 1 | 1 | 1 | 2 | 0 | 2 | 10 | 0.7 | 0.5 |
| 30554 | Control | 1 | 0 | 0 | 1 | 0 | 1 | 1 | 0 | 1 | 1 | 0 | 1 | 1 | 0 | 1 | 2 | 0 | 1 | 11 | 0.7 | |
| | | | | | | | | | | | | | | | | | Difference (test − control) | | | | 0.1 | |

ER = erythema
EX = exudate
ED = edema
CII = Cumulative Irritation Index

Figure 7

| Animal # | Group | Day 0 | | | Day 1 | | | Day 2 | | | Day 3 | | | Day 4 | | | Day 5 | | | Total | Irritation Score | CII |
|---|---|---|---|---|---|---|---|---|---|---|---|---|---|---|---|---|---|---|---|---|---|---|
| | | ER | EX | ED | ER | EX | ED | ER | EX | ED | ER | EX | ED | ER | EX | ED | ER | EX | ED | | | |
| 30547 | Test | 0 | 0 | 0 | 2 | 0 | 1 | 2 | 0 | 1 | 2 | 0 | 2 | 2 | 0 | 2 | 2 | 0 | 2 | 18 | 1.2 | |
| 30548 | Test | 0 | 0 | 0 | 1 | 0 | 0 | 1 | 0 | 1 | 2 | 0 | 2 | 2 | 0 | 2 | 1 | 0 | 1 | 13 | 0.9 | 0.8 |
| 30549 | Test | 0 | 0 | 0 | 0 | 0 | 0 | 0 | 0 | 0 | 1 | 0 | 1 | 1 | 0 | 1 | 1 | 0 | 0 | 5 | 0.3 | |
| 30519 | Control | 0 | 0 | 0 | 1 | 0 | 0 | 2 | 0 | 1 | 2 | 0 | 1 | 2 | 0 | 1 | 2 | 0 | 2 | 14 | 0.9 | |
| 30546 | Control | 0 | 0 | 0 | 0 | 0 | 0 | 0 | 0 | 0 | 1 | 0 | 1 | 2 | 0 | 1 | 2 | 0 | 2 | 9 | 0.6 | 0.7 |
| 30542 | Control | 1 | 0 | 0 | 1 | 0 | 0 | 1 | 0 | 0 | 1 | 0 | 1 | 1 | 0 | 1 | 1 | 0 | 0 | 7 | 0.5 | |
| | | | | | | | | | | | | | | | | | | | | Difference (test − control) | 0.1 | |

ER = erythema
EX = exudate
ED = edema
CII = Cumulative Irritation Index

Figure 8

Scoring Criteria

| Epithelium | Score | Leukocytes (per HPF*) | Score | Vascular Congestion | Score | Edema | Score |
|---|---|---|---|---|---|---|---|
| Intact | 0 | Absent | 0 | Absent | 0 | Absent | 0 |
| Cell degeneration or flattening | 1 | Minimal (<25) | 1 | Minimal | 1 | Minimal | 1 |
| Metaplasia | 2 | Mild (26-50) | 2 | Mild | 2 | Mild | 2 |
| Focal erosion | 3 | Moderate (51-100) | 3 | Moderate | 3 | Moderate | 3 |
| Generalized erosion | 4 | Marked (>100) | 4 | Marked | 4 | Marked | 4 |

*HPF = high power field (40X)

Figure 9A

| ANIMAL #: | TEST ARTICLE | | | CONTROL ARTICLE | | |
|---|---|---|---|---|---|---|
| | 30428 | 30439 | 30440 | 30424 | 30425 | 30426 |
| Epithelium | 0 | 0 | 0 | 0 | 0 | 0 |
| Leukocytes | 1 | 2 | 2 | 1 | 1 | 2 |
| Vascular Congestion | 0 | 1 | 0 | 2 | 1 | 1 |
| Edema | 0 | 0 | 0 | 0 | 0 | 0 |
| Total | 2 | 3 | 3 | 3 | 2 | 3 |
| Group Mean* | | 3 | | | 3 | |

Figure 9B

| Average Test Article Score | 3 |
|---|---|
| (-) Average Control Score | 3 |
| Irritant Rank Score | 0 |
| Interpretation of the Irritant Rank Score: | Non-irritant |

Figure 10A

| ANIMAL #: | TEST ARTICLE | | | CONTROL ARTICLE | | |
|---|---|---|---|---|---|---|
| | 30231 | 30233 | 30251 | 30086 | 30093 | 30427 |
| Epithelium | 0 | 0 | 0 | 0 | 0 | 0 |
| Leukocytes | 1 | 1 | 1 | 1 | 1 | 1 |
| Vascular Congestion | 1 | 1 | 2 | 1 | 1 | 1 |
| Edema | 0 | 0 | 0 | 0 | 0 | 0 |
| Total | 2 | 2 | 3 | 2 | 2 | 2 |
| Group Mean* | | 2 | | | 2 | |

Figure 10B

| Average Test Article Score | 2 |
|---|---|
| (-) Average Control Score | 2 |
| Irritant Rank Score | 0 |
| Interpretation of the Irritant Rank Score: | Non-irritant |

Figure 11A

| ANIMAL #: | TEST ARTICLE | | | CONTROL ARTICLE | | |
|---|---|---|---|---|---|---|
| | 30535 | 30536 | 30537 | 30539 | 30544 | 30545 |
| Epithelium | 0 | 0 | 0 | 0 | 0 | 0 |
| Leukocytes | 2 | 1 | 2 | 1 | 1 | 1 |
| Vascular Congestion | 1 | 1 | 1 | 1 | 1 | 1 |
| Edema | 0 | 0 | 0 | 0 | 0 | 0 |
| Total | 3 | 2 | 3 | 2 | 2 | 2 |
| Group Mean* | 3 | | | 2 | | |

Figure 11B

| | |
|---|---|
| Average Test Article Score | 3 |
| (-) Average Control Score | 2 |
| Irritant Rank Score | 1 |
| Interpretation of the Irritant Rank Score: | Minimal Irritant |

Figure 12A

| ANIMAL #: | CONTROL | | | | TEST ARTICLE | | |
|---|---|---|---|---|---|---|---|
| | 30559 | 30561 | 30562 | 30564 | 30565 | 30568 | |
| Epithelium | 0 | 0 | 0 | 1 | 3 | 0 | |
| Leukocytes | 2 | 1 | 2 | 1 | 2 | 1 | |
| Vascular Congestion | 1 | 0 | 1 | 0 | 2 | 1 | |
| Edema | 0 | 1 | 0 | 1 | 1 | 0 | |
| Total | 3 | 2 | 3 | 3 | 8 | 2 | |
| Group Mean* | 3 | | | | 4 | | |

Figure 12B

| Average Test Article Score | 4 |
|---|---|
| (-) Average Control Score | 3 |
| Irritant Rank Score | 1 |
| Interpretation of the Irritant Rank Score: | Minimal Irritant |

Figure 13A

| ANIMAL #: | TEST ARTICLE ||| CONTROL ARTICLE |||
|---|---|---|---|---|---|---|
| | 30555 | 30556 | 30557 | 30550 | 30553 | 30554 |
| Epithelium | 0 | 0 | 0 | 0 | 0 | 0 |
| Leukocytes | 1 | 2 | 1 | 2 | 1 | 1 |
| Vascular Congestion | 2 | 1 | 1 | 1 | 1 | 2 |
| Edema | 0 | 0 | 0 | 0 | 0 | 0 |
| Total | 3 | 3 | 2 | 3 | 2 | 3 |
| Group Mean* | | 3 | | | 3 | |

Figure 13B

| Average Test Article Score | 3 |
|---|---|
| (-) Average Control Score | 3 |
| Irritant Rank Score | 0 |
| Interpretation of the Irritant Rank Score: | Non-irritant |

Figure 14A

| ANIMAL #: | TEST ARTICLE | | | CONTROL ARTICLE | | |
|---|---|---|---|---|---|---|
| | 30547 | 30548 | 30549 | 30519 | 30542 | 30546 |
| Epithelium | 0 | 0 | 0 | 0 | 0 | 0 |
| Leukocytes | 1 | 2 | 2 | 1 | 2 | 1 |
| Vascular Congestion | 2 | 1 | 2 | 2 | 2 | 2 |
| Edema | 0 | 0 | 0 | 0 | 0 | 0 |
| Total | 3 | 3 | 4 | 3 | 4 | 3 |
| Group Mean* | 3 | | | 3 | | |

Figure 14B

| | |
|---|---|
| Average Test Article Score | 3 |
| (-) Average Control Score | 3 |
| Irritant Rank Score | 0 |
| Interpretation of the Irritant Rank Score: | Non-irritant |

Diagram of culture well with insert containing full-thickness EpiVaginal tissue.

FORMULATIONS FOR THE TREATMENT OF VAGINAL DISORDERS

This application claims priority to U.S. Provisional Application No. 61/839,070 filed Jun. 25, 2013, the entirety of which is incorporated herein by reference.

NAMES OF THE PARTIES TO A JOINT RESEARCH AGREEMENT

For purposes of 35 U.S.C. 102(c), a joint research agreement was executed between Mission Pharmacal and Université Laval in an invention relating to novel formulations for the treatment of vaginal disorders.

BACKGROUND OF THE INVENTION

Bacterial vaginosis (BV) is a common condition that is related to alterations in the normal vaginal flora. It is the most common cause of vaginitis in women and has a recurrence rate of approximately 20%-40% at one month after therapy. In addition to the general discomfort associated with the condition, BV has been linked to premature membrane rupture, premature delivery, low birth weight, acquisition of HIV and other STDs, development of pelvic inflammatory disease (PID), and post-operative infections following gynecological procedures.

Although the precise etiology of BV is unknown, the disease itself is associated with the decrease or absence of protective lactobacilli which are normally present in the vagina. Lactobacilli produce lactic acid from glycogen to maintain the vagina's acidic pH. This acidic environment inhibits the growth of other bacterial species typically found in the vagina, albeit at low levels. Vaginal lactobacilli also produce hydrogen peroxide ($H_2O_2$), which is toxic to viruses as well as to bacteria in vitro. When lactobacilli are sufficiently absent, bacteria such as Gardnerella vaginalis, Bacteroides spp., Mobiluncus spp., Haemophilus spp., peptostreptococci, Mycoplasma hominis, ureaplasma, and other anaerobes can populate the vaginal tract without difficulty.

Currently approved treatments for BV include administering metronidazole ("MTZ") 500 mg orally twice a day for 7 days; administering MTZ gel 0.75%, one full applicator (5 g) intravaginally, once a day for 5 days; administering clindamycin cream 2%, one full applicator (5 g) intravaginally at bedtime for 7 days; administering tinidazole, 2 g orally once daily for 2 days; or administering tinidazole, 1 g orally once daily for 5 days.

Although MTZ remains the primary choice for treating BV in the United States, tinidazole is particularly useful for treating MTZ-resistant G. vaginalis, an organism commonly associated with BV. Despite this utility, tinidazole must be dosed orally, whereas MTZ can be dose intravaginally. Common side effects associated with the oral administration of tinidazole include, but are not limited to, metallic/bitter taste, nausea, anorexia, dyspepsia/cramps/epigastric discomfort, vomiting, constipation, tongue discoloration, stomatitis, diarrhea, decreased appetite, and flatulence.

Thus, there exists a need for novel tinidazole formulations suitable for the treatment of BV and other diseases of the vaginal cavity that respond to or are susceptible to tinidazole (e.g. trichomoniasis) that reduce or alleviate many of the side effects commonly associated with the oral form of the drug. The present disclosure provides such formulations.

BRIEF SUMMARY OF THE INVENTION

The present disclosure provides formulations suitable for the intravaginal delivery of tinidazole to a subject in need thereof, the formulations comprising water, tinidazole, a thermoreversible gelling agent, one or more pharmaceutically acceptable $C_1$-$C_7$ alcohols, a solubility enhancer, and, optionally, one or more preservatives.

In some embodiments, the thermoreversible gelling agent is triblock copolymer having a central hydrophobic block flanked on each side with a hydrophilic block. In certain embodiments, the hydrophobic block is polypropylene oxide). In some embodiments, the hydrophilic block is poly(ethylene oxide).

In some embodiments, the thermoreversible gelling agent is poloxamer 407.

In some embodiments, the one or more pharmaceutically acceptable $C_1$-$C_7$ alcohols comprise a first pharmaceutically acceptable $C_1$-$C_7$ alcohol and a second pharmaceutically acceptable $C_1$-$C_7$ alcohol. In some embodiments, the first and second pharmaceutically acceptable $C_1$-$C_7$ alcohols are independently selected from the group consisting of methanol, ethanol, isopropanol, propylene glycol, 2-(2-ethoxyethoxy)ethanol, benzyl alcohol, and combinations thereof.

In some embodiments, the first pharmaceutically acceptable $C_1$-$C_7$ alcohol is benzyl alcohol.

In certain embodiments, the second pharmaceutically acceptable $C_1$-$C_7$ alcohol is isopropanol.

In some embodiments, the isopropanol is a 60% (w/w) solution in water.

In some embodiments, the solubility enhancer is selected from the group consisting of mono- and di-alkyl ethers of isosorbide. In some embodiments, the mono- or di-alkyl ether of isosorbide is dimethyl isosorbide.

In certain embodiments, the water comprises a mixture of sterile deionized water and a buffered aqueous solution. In certain embodiments, the buffered aqueous solution is citrate buffer.

In some embodiments, the formulation has a buffered pH selected from the group consisting of about 3 to about 5, about 3.5 to about 4.5, and about 4 to about 4.5.

In certain embodiments, the tinidazole comprises from about 0.1 to about 2% (w/w) of the formulations and in certain embodiments, the tinidazole comprises about 1%, about 1.25%, or about 1.5% (w/w) of the formulations.

In some embodiments, the formulations comprise about 20% poloxamer 407 (w/w), about 49.6% citrate buffer (w/w), about 3.1% benzyl alcohol (w/w), about 12% (w/w) of a 60% (w/w) solution of isopropanol in water, about 13.8% dimethylisosorbide (w/w), and about 1.5% tinidazole.

In other embodiments, the formulations comprise about 19% poloxamer 407 (w/w), about 53% citrate buffer (w/w), about 2.9% benzyl alcohol (w/w), about 11% (w/w) of a 60% (w/w) solution of isopropanol in water, about 12.7% dimethylisosorbide (w/w), and about 1.25% tinidazole.

In still further embodiments, the formulations comprise about 18% poloxamer 407 (w/w), about 57% citrate buffer (w/w), about 2.5% benzyl alcohol (w/w), about 10% of a 60% (w/w) solution of isopropanol in water, about 11.5% dimethylisosorbide (w/w), and about 1% tinidazole.

In other embodiments, the present disclosure provides methods for treating bacterial vaginosis, trichomoniasis, or other diseases of the vaginal cavity susceptible to tinidazole, comprising intravaginally administering to a subject in need thereof a formulation comprising water, tinidazole, a thermoreversible gelling agent, one or more pharmaceutically acceptable $C_1$-$C_7$ alcohols, a solubility enhancer, and, optionally, one or more preservatives.

In certain embodiments of the methods described herein, the thermoreversible gelling agent is triblock copolymer having a central hydrophobic block flanked on each side with a hydrophilic block. In certain embodiments of the methods described herein, the hydrophobic block is poly-propylene oxide). In some embodiments of the methods described herein, the hydrophilic block is poly(ethylene oxide). In certain embodiments of the methods described herein, the thermoreversible gelling agent is poloxamer 407.

In certain embodiments of the methods described herein, the one or more pharmaceutically acceptable $C_1$-$C_7$ alcohols comprises a first pharmaceutically acceptable $C_1$-$C_7$ alcohol and a second pharmaceutically acceptable $C_1$-$C_7$ alcohol. In some embodiments of the methods described herein, the first and second pharmaceutically acceptable $C_1$-$C_7$ alcohols are selected from the group consisting of methanol, ethanol, isopropanol, propylene glycol, 2-(2-ethoxyethoxy)ethanol, benzyl alcohol, and combinations thereof. In other embodiments of the methods described herein, the first pharmaceutically acceptable $C_1$-$C_7$ alcohol is benzyl alcohol. In some embodiments of the methods described herein, the second pharmaceutically acceptable $C_1$-$C_7$ alcohol is isopropanol. In certain embodiments of the methods described herein, the isopropanol is a 60% (w/w) solution in water.

In some embodiments of the methods described herein, the solubility enhancer is selected from the group consisting of mono- and di-alkyl ethers of isosorbide. In some embodiments, the mono- or di-alkyl ether of isosorbide is dimethyl isosorbide.

In certain embodiments of the methods described herein, the water comprises a mixture of sterile deionized water and a buffered aqueous solution. In certain embodiments of the methods described herein, the buffered aqueous solution is citrate buffer.

In some of the embodiments of the methods disclosed herein, the formulation has a buffered pH selected from the group consisting of about 3 to about 5, about 3.5 to about 4.5, and about 4.

In certain embodiments of the methods described herein, the tinidazole comprises from about 0.1% to about 2% (w/w) of the formulation. In other embodiments of the methods described herein, the tinidazole comprises about 1%, about 1.25%, or about 1.5% (w/w) of the formulation.

In certain embodiments of the methods described herein, the subject is a human.

The present disclosure also relates to a pharmaceutical composition comprising: about 18-20% poloxamer 407 (w/w), about 49.6-57% citrate buffer (w/w), about 2.5-3.1% benzyl alcohol (w/w), about 10-12% (w/w) of a 60% (w/w) solution of isopropanol in water, about 11.5%-13.8% dimethylisosorbide (w/w), and about 1-1.5% tinidazole (w/w) (and/or an active metabolite thereof), for treating bacterial vaginosis, trichomoniasis, or other disease(s) of the vaginal cavity susceptible to tinidazole.

In certain embodiments the pharmaceutical composition exists as a viscous liquid at room temperature and gels at or close to body temperature.

The present disclosure further relates to the use of the formulations as described herein for treating bacterial vaginosis, trichomoniasis, or other disease(s) of the vaginal cavity susceptible to tinidazole.

The present disclosure relates also to the use of the formulations as described herein for the manufacture of a medicament for the treatment of bacterial vaginosis, trichomoniasis, or other disease of the vaginal cavity susceptible to tinidazole.

An additional aspect of the present disclosure relates to a method for treating a vaginal infection comprising intravaginally administering to the subject a formulation containing about 0.1-2% tinidazole, or an active metabolite thereof.

An additional aspect of the present disclosure relates to a method for administering tinidazole to a human subject, comprising obtaining a formulation containing about 0.1-2% tinidazole, or an active metabolite thereof, wherein said formulation exists as a viscous liquid at room temperature; and intravaginally administering the formulation to a human subject, wherein the formulation gels at or close to body temperature.

In a further embodiment, the present disclosure provides a formulation suitable for the intravaginal delivery of tinidazole to a human subject in need thereof, the formulation comprising tinidazole, wherein the formulation has a Franz cell flux of from about 2 to about 10 $(\mu mol/cm^2)/\sqrt{t}(h)$.

In some embodiments, the Franz cell flux is from about 6 to about 9 $(\mu mol/cm^2)/\sqrt{t}(h)$.

In another embodiment, the present disclosure provides a formulation suitable for the intravaginal delivery of tinidazole to a human subject in need thereof, the formulation comprising tinidazole, wherein the formulation has a mean flux rate in EpiVaginal™ tissue of from about 15 nmol/cm²/min to about 30 nmol/cm²/min.

In certain embodiments, the mean flux rate in EpiVaginal™ tissue is from about 18 nmol/cm²/min to about 22.5 nmol/cm²/min.

The present disclosure also provides a formulation suitable for the intravaginal delivery of tinidazole to a human subject in need thereof, the formulations comprising tinidazole, wherein the formulation has a mean tinidazole receiver fluid concentration at 1 hour of from about 0.5 mM to about 2.5 mM.

In some embodiments, the formulation has a mean tinidazole receiver fluid concentration at 1 hour of from about 1.14 mM to about 1.74 mM.

The present disclosure also provides a tinidazole gel formulation suitable for the intravaginal delivery of tinidazole to a subject in need thereof, the formulation comprising water, tinidazole, a thermoreversible gelling agent, one or more pharmaceutically acceptable $C_1$-$C_7$ alcohols, a solubility enhancer, and, optionally, one or more preservatives, the tinidazole gel formulation prepared by the process of a) dissolving the thermoreversible gelling agent in the water to form a first solution; b) combining the one or more pharmaceutically acceptable $C_1$-$C_7$ alcohols, the solubility enhancer, and the tinidazole to form a second solution; and c) adding the second solution to the first solution.

In certain embodiments, the thermoreversible gelling agent is triblock copolymer having a central hydrophobic block flanked on each side with a hydrophilic block.

In certain embodiments, the hydrophobic block is polypropylene oxide).

In certain embodiments, the hydrophilic block is poly (ethylene oxide).

In certain embodiments, the thermoreversible gelling agent is poloxamer 407.

In some embodiments, the one or more pharmaceutically acceptable $C_1$-$C_7$ alcohols comprise a first pharmaceutically acceptable $C_1$-$C_7$ alcohol and a second pharmaceutically acceptable $C_1$-$C_7$ alcohol.

In some embodiments, the first and second pharmaceutically acceptable $C_1$-$C_7$ alcohols are independently selected from the group consisting of methanol, ethanol, isopropanol, propylene glycol, 2-(2-ethoxyethoxy)ethanol, benzyl alcohol, and combinations thereof.

In certain embodiments, the first pharmaceutically acceptable $C_1$-$C_7$ alcohol is benzyl alcohol.

In some embodiments, the second pharmaceutically acceptable $C_1$-$C_7$ alcohol is isopropanol. In certain embodiments, the isopropanol is a 60% (w/w) solution in water.

In some embodiments, the solubility enhancer is selected from the group consisting of mono- and di-alkyl ethers of isosorbide. In certain embodiments, the mono- or di-alkyl ether of isosorbide is dimethyl isosorbide.

In some embodiments, the water comprises a mixture of deionized water and a buffered aqueous solution. In particular embodiments, the buffered aqueous solution is citrate buffer.

In certain embodiments, the formulation has a pH of from about 3 to about 5. In other embodiments, the formulation has a pH of from about 3.5 to about 4.5.

The present disclosure further provides a process for the preparation of a tinidazole gel formulation suitable for the intravaginal delivery of tinidazole to a human subject in need thereof, the process comprising a) dissolving a thermoreversible gelling agent in water to form a first solution; b) combining one or more pharmaceutically acceptable $C_1$-$C_7$ alcohols, a solubility enhancer, and tinidazole to form a second solution; and c) adding the second solution to the first solution.

In certain embodiments, the thermoreversible gelling agent is triblock copolymer having a central hydrophobic block flanked on each side with a hydrophilic block.

In some embodiments, the hydrophobic block is polypropylene oxide).

In some embodiments, the hydrophilic block is poly(ethylene oxide).

In some embodiments, the thermoreversible gelling agent is poloxamer 407.

In some embodiments, the one or more pharmaceutically acceptable $C_1$-$C_7$ alcohols comprise a first pharmaceutically acceptable $C_1$-$C_7$ alcohol and a second pharmaceutically acceptable $C_1$-$C_7$ alcohol.

In some embodiments, the first and second pharmaceutically acceptable $C_1$-$C_7$ alcohols are independently selected from the group consisting of methanol, ethanol, isopropanol, propylene glycol, 2-(2-ethoxyethoxy)ethanol, benzyl alcohol, and combinations thereof.

In some embodiments, the first pharmaceutically acceptable $C_1$-$C_7$ alcohol is benzyl alcohol.

In certain embodiments, the second pharmaceutically acceptable $C_1$-$C_7$ alcohol is isopropanol. In some embodiments, the isopropanol is a 60% (w/w) solution in water.

In certain embodiments, the solubility enhancer is selected from the group consisting of mono- and di-alkyl ethers of isosorbide. In some embodiments, the mono- or di-alkyl ether of isosorbide is dimethyl isosorbide.

In some embodiments, the water comprises a mixture of deionized water and a buffered aqueous solution. In certain embodiments, the buffered aqueous solution is citrate buffer.

In some embodiments, the formulation has a mean tinidazole receiver fluid concentration at 2 hours of from about 1.5 mM to about 3.5 mM.

In other embodiments, the formulation has a mean tinidazole receiver fluid concentration at 4 hours of from about 3 mM to about 6 mM.

In other embodiments, the formulation has a mean tinidazole receiver fluid concentration at 2 hours of from about 2.3 mM to about 2.6 mM.

In some embodiments, the formulation has a mean tinidazole receiver fluid concentration at 4 hours of from about 4 mM to about 5.5 mM.

The present disclosure further provides a tinidazole gel formulation prepared by any of the processes described herein.

The present disclosure further provides a tinidazole gel formulation that does not inhibit or only minimally inhibits *lactobacillus* strains at a tinidazole concentration sufficient to inhibit *Gardnerella vaginalis* strains associated with bacterial vaginosis.

BRIEF DESCRIPTION OF THE DRAWINGS/FIGURES

The foregoing summary, as well as the following detailed description of the embodiments, will be better understood when read in conjunction with the appended drawings. For the purpose of illustration, the drawings may describe the use of specific embodiments. It should be understood, however, that the formulations described herein are not limited to the precise embodiments discussed or described in the figures.

FIG. 1 describes the standard for visually evaluating rabbit vaginal tissue exposed to the formulations described herein.

FIG. 2 describes the observed effects of vehicle formulation V1 on external rabbit vaginal tissue.

FIG. 3 describes the observed effects of vehicle formulation V2 on external rabbit vaginal tissue.

FIG. 4 describes the observed effects of vehicle formulation V3 on external rabbit vaginal tissue.

FIG. 5 describes the observed effects of formulation F1 on external rabbit vaginal tissue.

FIG. 6 describes the observed effects of formulation F2 on external rabbit vaginal tissue.

FIG. 7 describes the observed effects of formulation F3 on external rabbit vaginal tissue.

FIG. 8 describes the evaluation standard for histopathological analysis of explanted rabbit vaginal tissue.

FIGS. 9A and 9B describe the observation and results of histopathological evaluation of rabbit vaginal explants previously treated with vehicle formulation V1.

FIGS. 10A and 10B describe the observation and results of histopathological evaluation of rabbit vaginal explants previously treated with vehicle formulation V2.

FIGS. 11A and 11B describe the observation and results of histopathological evaluation of rabbit vaginal explants previously treated with vehicle formulation V3.

FIGS. 12A and 12B describe the observation and results of histopathological evaluation of rabbit vaginal explants previously treated with formulation F1.

FIGS. 13A and 13B describe the observation and results of histopathological evaluation of rabbit vaginal explants previously treated with formulation F2.

FIGS. 14A and 14B describe the observation and results of histopathological evaluation of rabbit vaginal explants previously treated with formulation F3.

DETAILED DESCRIPTION OF THE INVENTION

Figure 15:
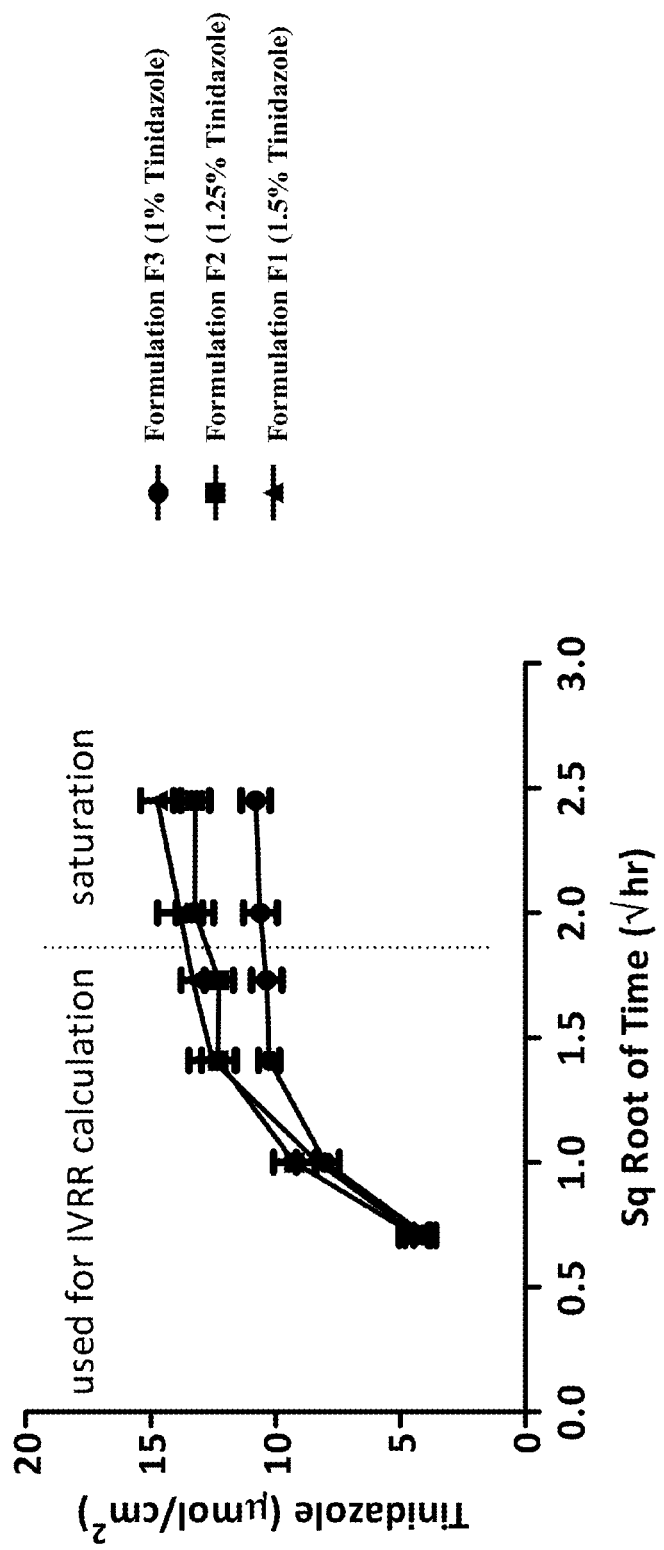
FIG. 15 is a graphical representation of the mean±SD of tinidazole released from formulations F1, F2, and F3 in Franz cell studies.

The articles "a," "an," and "the" are used herein to refer to one or more than one (i.e., to at least one) of the grammatical object of the article. By way of example, "an element" means one element or more than one element.

The phrase "substantially free of" as used herein means less than 5%, less than 2.5%, less than 1%, less than 0.1%, less than 0.01%, or less than 0.001% of a given component in the formulations described herein.

As used herein, "administration" or "administering" to a subject includes, but is not limited to, the act of a physician or other medical professional prescribing a pharmaceutical composition of the invention for a subject.

Throughout the specification, the present disclosure provides certain ranges and certain sub-ranges within those ranges. The identification of certain sub-ranges notwithstanding, the present disclosure should be read to include and disclose all sub-ranges within a given range (or sub-range). For example, if a range of 1 to 20 is described herein and a sub-range of 5 to 15 is also described, the present disclosure should be understood to include and disclose all other sub-ranges within the originally defined range and sub-range, e.g., 1 to 5, 7 to 12, 15 to 20, 2 to 18, etc.

The present disclosure provides novel aqueous tinidazole formulations suitable for intravaginal administration to a subject in need thereof. In particular embodiments, the formulations can comprise water, tinidazole or an active metabolite thereof, a thermoreversible gelling agent, one or more pharmaceutically acceptable $C_1$-$C_7$ alcohols, a solubility enhancer, and, optionally, one or more preservatives. In certain embodiments, the formulations can further include a polyol, such as, but not limited to polyethylene glycol, an optional penetration enhancer, or an optional excipient such as HPMC. In particular embodiments, the formulations can be completely or substantially free of boric acid and/or ethylenediaminetetraacetic acid (EDTA). In certain embodiments, the formulations can be free or substantially free of a second active ingredient, such that tinidazole is the only active ingredient in the formulations.

An important characteristic of the formulations described herein are their thermoreversible nature. In particular embodiments, the formulations exist as a viscous liquid at room temperature (i.e. about 20° C. to about 23° C.). At higher temperatures, though, the formulations can exist as a gel. In particular embodiments, the formulations can be a gel at or close to body temperature (i.e. about 35° C. to about 37° C.). Without wishing to be bound to any particular theory, it is believed that gel formation at higher temperature is a useful property because it allows the formulations to flow into the vaginal cavity and to reach the smallest irregularities of the mucosal surface where they subsequently gel and adhere to biological surfaces such as the vaginal epithelia.

Although using thermoreversible gels for the prevention of STDs was previously disclosed, see, e.g. WO 97/42962 and WO 99/53897 (both of which are hereby incorporated by reference in their entirety), neither publication teaches the use of tinidazole. Moreover it has now been unexpectedly discovered that the percentage of tinidazole in a formulation including a thermoreversible gelling agent can be significantly increased using the formulations disclosed herein.

In certain embodiments, tinidazole can be used in the formulations described herein at any suitable concentration. In other embodiments, the concentration of tinidazole can be about 0.1% to about 2% (w/w), about 0.5% to about 2% (w/w), or about 0.75% to about 2% (w/w). In particular embodiments, the concentration of tinidazole can be about 0.75 to about 1.5% (w/w). In specific embodiments, the concentration of tinidazole can be about 1%, about 1.25%, or about 1.5% (w/w). The formulations can also include an active metabolite of tinidazole at any suitable concentration. Known active metabolites of tinidazole include, but are not limited to 1-(2-(ethylsulfonyl)ethyl)-2-methyl-4-nitro-1H-imidazol-5-ol and 2-hydroxymethyl tinidazole.

In certain embodiments, the thermoreversible gelling agent can be present in the formulations described herein at any suitable concentration. In certain embodiments, the thermoreversible gelling agent can be at a concentration of about 5% to about 50% (w/w) and in certain embodiments, at a concentration of about 15% to about 35% (w/w). In particular embodiments, the thermoreversible gelling agent can be present at a concentration of about 15% to about 25% (w/w). In certain embodiments, the thermoreversible gelling agent can be present in an amount ranging from about 15% to about 25% (w/w); in an amount ranging from about 17% to about 22% (w/w); or in an amount ranging from about 18% to about 20% (w/w). In certain embodiments, the thermoreversible gelling agent can be present at a concentration of about 18% (w/w), about 19% (w/w), or about 20% (w/w). Exemplary thermoreversible gelling agents include, but are not limited to, triblock copolymers having a central hydrophobic block flanked on each side with a hydrophilic block. In certain embodiments the hydrophobic block can be a block of polypropylene oxide). In certain embodiments, the hydrophilic blocks can be blocks of poly(ethylene oxide). In particular embodiments, the thermoreversible gelling agent can be selected from the group consisting of poloxamer 407 (CAS 9003-11-6), poloxamer 124, poloxamer 188, poloxamer 237, poloxamer 338. In specific embodiments, the thermoreversible gelling agent is poloxamer 407.

The one or more pharmaceutically acceptable $C_1$-$C_7$ alcohols can be present in the formulations at any suitable concentration and can include any appropriate straight chain, branched, cyclic, or aromatic alcohol having the designated number of carbons. Exemplary pharmaceutically acceptable $C_1$-$C_7$ alcohols include, but are not limited to, ethanol, isopropanol, propylene glycol, 2-(2-ethoxyethoxy) ethanol, and benzyl alcohol. In certain embodiments, the one or more pharmaceutically acceptable $C_1$-$C_7$ alcohols can be present at a concentration of about 2% to about 20% (w/w). In other embodiments, the one or more pharmaceutically acceptable $C_1$-$C_7$ alcohols can be present at a concentration of about 5% to about 15% (w/w). In particular embodiments, the one or more pharmaceutically acceptable $C_1$-$C_7$ alcohols can be present from about 8% to about 11% (w/w).

In certain embodiments, the one or more pharmaceutically acceptable $C_1$-$C_7$ alcohols can include one to ten, i.e. 1, 2, 3, 4, 5, 6, 7, 8, 9 or 10 pharmaceutically acceptable $C_1$-$C_7$ alcohols. In certain embodiments, the formulations can include a first $C_1$-$C_7$ alcohol and a second $C_1$-$C_7$ alcohol. In certain embodiments the first $C_1$-$C_7$ alcohol can be present at a concentration of about 2.25% to about 3.25% (w/w). In certain embodiments, the first $C_1$-$C_7$ alcohol can be present in an amount of about 2.5%, about 2.9%, or about 3.2% (w/w). In other embodiments, the second $C_1$-$C_7$ alcohol can be present at a concentration of about 10% to about 12% (w/w), and in certain embodiments can be about 6%, about 6.5%, or about 7.2% (w/w) of the formulation. In certain embodiments, the first $C_1$-$C_7$ alcohol can be benzyl alcohol. In certain embodiments, the second $C_1$-$C_7$ alcohol can be isopropyl alcohol. In certain embodiments, the isopropyl alcohol can be a 60% solution (w/w) in water.

The formulations can also include a solubility enhancer, useful for enhancing the solubility of tinidazole in the formulation. Exemplary solubility enhancers include, but are not limited to, mono and di-alkyl ethers of isosorbide. In particular embodiments, the solubility enhancer is dimethylisosorbide ("DMI"). The solubility enhancer can be present in the formulations at any suitable concentration; however, in certain embodiments it can be present at a concentration of about 10% to about 15% (w/w). In other embodiments, the solubility enhancer can be present at a concentration of about 11.5%, about 12.7%, or about 14% (w/w).

The formulations can further include an optional penetration enhancer. The optional penetration enhancer can be used in the formulations in any suitable concentration; however in certain embodiments, it can be present in the formulations in a range of about 0.01% to 15% (w/w). Exemplary penetration enhancers include, but are not limited to terpenes and terpenoids (such as menthol and the like); pyrrolidones (such as N-methyl-2-pyrrolidone, 1-dodecylazacycloheptan-2-one, and the like); sulfoxides (such as DMSO and the like); phospholipids; cyclodextrins such as, but not limited to, β-cyclodextrin; dodecyl-N,N-dimethylamino acetate; clofibric acid; and amino acid derivatives such as, but not limited to, dodecyl N,N-dimethylamino isopropionate. While in certain embodiments the optional penetration enhancer can be present, in other embodiments, the penetration enhancer can be completely or substantially absent.

The formulations can optionally include one or more preservatives in a pharmaceutically acceptable amount. Suitable exemplary preservatives include, but are not limited to, methylparaben, propylparaben, BHA, BHT, and combinations of the foregoing. In certain embodiments, the formulations can comprise less than about 1% (w/w), less than about 0.5% (w/w), or less than about 0.05% (w/w) of the formulation.

In typical embodiments, the remainder of the formulations comprises water. As used herein "water" refers to sterile deionized water, buffered aqueous solutions comprising sterile deionized water, or any combination of the foregoing. The amount of water in the formulations can be at least about 10%, 20%, 30%, 40%, 45%, 47%, 50%, 55%, 58%, 60%, 61%, 65% or at least about 70% (w/w). In certain embodiments, the amount of water in the formulations can range from about 40% (w/w) to about 70% (w/w), from about 50% to about 70% (w/w), or from about 50% to about 65% (w/w). In particular embodiments, the amount of water in the formulations can be about 54.4% (w/w), about 57.6% (w/w), or about 61% (w/w).

Buffered aqueous solutions can contain one or more pharmaceutically acceptable buffering agents suitable for maintaining the pH of the formulations in a range of about 3 to about 5, and in certain embodiments, about 3.5 to about 4.5. Suitable buffering agents and systems are well known to those of ordinary skill in the art; however in certain embodiments, the buffering agent is a citrate buffer. Other possible buffering agents include, but are not limited to, veronal acetate buffer, and acetate buffer. In particular embodiments, the pH of the formulations is buffered to a pH of about 4 to about 4.5.

The viscosity of the formulations can range from about 1 cP to about 100,000 cP, about 1 cP to about 50,000 cP, about 1 cP to about 10,000 cP, or about 1 cP to about 1,000 cP in its ungelled state when measured using a Brookfield DV-II+ Pro Extra LV™ viscometer with spindle type 63 at 100 RPM at about 21° C. to about 22° C. In particular embodiments, the ungelled formulations can have a viscosity of about 1 to about 900 cP. In certain embodiments, the ungelled formulations can have a viscosity of about 200 cP to about 750 cP, and in other embodiments, the ungelled formulations can have a viscosity of about 300 cP to about 550 cP. In particular embodiments, the composition can have a viscosity of about 315 cP to about 345 cP. In other embodiments, the ungelled formulations can have a viscosity of about 420 cP to about 460 cP. In still other embodiments, the formulations can have a viscosity in the ungelled state of about 480 cP to about 550 cP.

In certain embodiments, the formulations can have a temperature of gelation ($T_{gel}$) of about 18 to about 37° C. In other embodiments, the formulations can have a $T_{gel}$ of about 22 to about 35° C. In still further embodiments, the formulations can have a $T_{gel}$ of about 30° C. to about 35° C. And in still other embodiments, the formulations can have a $T_{gel}$ of about 32° C.

In addition to providing the formulations discussed above, the present disclosure also provides methods for treating BV, trichomoniasis, or other disease or disorder suitable for treatment via the intravaginal administration of a tinidazole. Suitable methods for treating BV include intravaginally administering the formulations to a subject in need thereof. Exemplary subjects include mammals, preferably humans. In certain embodiments, the formulations can be administered intravaginally once a day for a period of up to about 30 days. However, in other embodiments, the formulations can be administered chronically over a period of months or years.

In certain embodiments, the formulations can be administered intravaginally twice a day for a period of up to about 30 days. In specific embodiments, the formulations can be administered intravaginally once or twice a day for a period of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In some embodiments, the formulations can be administered intravaginally once or twice a day every other day, once or twice a day every third day, once or twice a day every fourth day, once or twice a day every fifth day, once or twice a day every sixth day, once or twice a day once a week, once or twice a day one time every other week, once or twice a day one time every third week, once or twice a day once a month. In certain embodiments, the formulations can be administered intravaginally in a single application, i.e., in the substantial absence of further dosing until such time as symptoms recur or until the subject is directed by a physician to resume treatment.

The present formulations also have surprising stability at low temperature. For example, in certain embodiments, the formulations will show little or no tinidazole crystallization when chilled to as low as about 6° C. for 24 hours and then warmed to 22 C for 24 hours. In other embodiments, the formulations will show little or no tinidazole crystallization when chilled to as low as about 14° C. for 24 hours and then warmed to 22° C. for 24 hours.

The present formulations similarly exhibit unexpected long-term stability at 22° C., showing little or no tinidazole crystallization at 1, 2, and in certain embodiments 2.6 or 2.8 months. In other embodiments the formulations can be stable for at least about 10 months, at least about 12 months, and in other embodiments, at least about 18 months.

The present formulations have similarly shown a surprising lack of irritation in a rabbit vaginal model, as described in detail below.

In addition to the properties noted above, the formulations described herein can exhibit a "Franz cell flux." As used herein, a "Franz cell flux" refers to the rate at which tinidazole in the formulations described herein crosses a polycarbonate membrane having 0.40 µm pores and an area of 1.77 cm$^2$ in a Franz cell diffusion study at 37° C. wherein the receiver fluid is 0.05 M citrate buffer (pH 3.3). In some embodiments, Franz cell flux can range from about 2 to about 15 (µmol/cm$^2$)/√t, where t is measured in hours ("√t(h)"). In other embodiments, the Franz cell flux can range from about 4 to about 10 (µmol/cm$^2$)/√t. In still further embodiments, the Franz cell flux can range from about 6 to about 9 (µmol/cm$^2$)/√t(h). In particular embodiments, the Franz cell flux can be about 6, about 7.5, or about 8.7 (µmol/cm$^2$)/√t(h). In particular embodiments, the formulations can be any of formulations F1, F2, or F3 described elsewhere herein.

In other embodiments, Franz cell flux can range from 2 to 15 (µmol/cm$^2$)/√t(h). In other embodiments, the Franz cell flux can range from 4 to 10 (µmol/cm$^2$)/√t(h). In still further embodiments, the Franz cell flux can range from 6 to 9 (µmol/cm$^2$)/√t(h). In particular embodiments, the Franz cell flux can be 6, 7.5, or 8.7 (µmol/cm$^2$)/√t(h). In particular embodiments, the formulations can be any of formulations F1, F2, or F3 described elsewhere herein.

The formulations described herein can further exhibit a mean flux rate in EpiVaginal™ tissue culture. The "mean flux rate in EpiVaginal™ tissue culture" refers to the rate at which tinidazole in a 100 µL aliquot of the formulations described herein at 37° C. crosses a full thickness tissue culture produced from normal human-derived vaginal-ectocervical epithelial cells (VEC-100-FT EpiVaginal™ tissue available from MatTek Corporation, Ashland, Mass.), mounted on polycarbonate membranes having 0.4 µm pores, wherein the culture medium (alternatively referred to as the receiver fluid) is 0.5 ml VEC-100-ASY available from MatTek Corporation (Ashland, Mass.).

In particular embodiments, the mean flux rate (nmol/cm$^2$/min) can range from about 15 nmol/cm$^2$/min to about 30 nmol/cm$^2$/min. In other embodiments, the mean flux rate can range from about 15 nmol/cm$^2$/min to about 25 nmol/cm$^2$/min. In other embodiments, the mean flux rate can range from about 17 nmol/cm$^2$/min to about 25 nmol/cm$^2$/min. In other embodiments, the mean flux rate can range from about 18 nmol/cm$^2$/min to about 22.5 nmol/cm$^2$/min. In particular embodiments, the mean flux rate can be about 18, about 19, or about 22.5 nmol/cm$^2$/min.

In other embodiments, the mean flux rate (nmol/cm$^2$/min) can range from 15 nmol/cm$^2$/min to 30 nmol/cm$^2$/min; from 15 nmol/cm$^2$/min to 25 nmol/cm$^2$/min; from 17 nmol/cm$^2$/min to 25 nmol/cm$^2$/min; or from 18 nmol/cm$^2$/min to 22.5 nmol/cm$^2$/min. In particular embodiments, the mean flux rate can be 18, 19, or 22.5 nmol/cm$^2$/min.

The formulations described herein can also have a mean tinidazole receiver fluid concentration. The "mean tinidazole receiver fluid concentration" is the concentration of tinidazole in receiver fluid at a given time point after application of a 100 µL aliquot of the formulations described herein at 37° C. to full thickness tissue culture produced from normal human-derived vaginal-ectocervical epithelial cells (VEC-100-FT EpiVaginal™ tissue available from MatTek Corporation, Ashland, Mass.), mounted on polycarbonate membranes having 0.4 µm pores, wherein the culture medium/receiver fluid is VEC-100-ASY available from MatTek Corporation (Ashland, Mass.).

In particular embodiments, the mean tinidazole receiver fluid concentration after 1 hour can be about 0.5 mM to about 2.5 mM. In other embodiments, the mean tinidazole receiver fluid concentration after 1 hour can be about 1 mM to about 2 mM. In still other embodiments, the mean tinidazole receiver fluid concentration after 1 hour can be about 1.14 mM to about 1.74 mM. In particular embodiments, the mean tinidazole receiver fluid concentration after 1 hour can be about 1.14 mM, about 1.5 mM, or about 1.74 mM.

In other embodiments, the mean tinidazole receiver fluid concentration after 1 hour can range from 0.5 mM to 2.5 mM; from 1 mM to 2 mM; or from 1.14 mM to 1.74 mM. In particular embodiments, the mean tinidazole receiver fluid concentration after 1 hour can be 1.14 mM, 1.5 mM, or 1.74 mM.

In particular embodiments, the mean tinidazole receiver fluid concentration after 2 hours can be about 1.5 mM to about 3.5 mM. In other embodiments, the mean tinidazole receiver fluid concentration after 2 hours can be about 2 mM to about 3 mM. In still other embodiments, the mean tinidazole receiver fluid concentration after 2 hours can be about 2.3 mM to about 2.6 mM. In particular embodiments, the mean tinidazole receiver fluid concentration after 2 hours can be about 2.3 mM, about 2.9 mM, or about 2.6 mM.

In other embodiments, the mean tinidazole receiver fluid concentration after 2 hours can range from 1.5 mM to 3.5 mM; from 2 mM to 3 mM; or from 2.3 mM to 2.6 mM. In particular embodiments, the mean tinidazole receiver fluid concentration after 2 hours can be 2.3 mM, 2.9 mM, or 2.6 mM.

In other embodiments, the mean tinidazole receiver fluid concentration after 4 hours can be about 3.5 mM to about 6 mM. In other embodiments, the mean tinidazole receiver fluid concentration after 4 hours can be about 4 mM to about 5.5 mM. In particular embodiments, the mean tinidazole receiver fluid concentration after 4 hours can be about 4.4 mM, about 5.6 mM, or about 5.1 mM.

In other embodiments, the mean tinidazole receiver fluid concentration after 4 hours can range from 3.5 mM to 6 mM or from 4 mM to 5.5 mM. In particular embodiments, the mean tinidazole receiver fluid concentration after 4 hours can be 4.4 mM, 5.6 mM, or 5.1 mM.

The formulations described herein can also have a concentration dependent mean peak tinidazole concentration in EpiVaginal™ tissue ("mean peak concentration"). The mean peak concentration is the average maximum concentration of tinidazole in full thickness tissue culture produced from normal human-derived vaginal-ectocervical epithelial cells (VEC-100-FT EpiVaginal™ tissue available from MatTek Corporation, Ashland, Mass.) after application of a 100 µL aliquot of the formulations described herein at 37° C. for a period of time sufficient to achieve the maximum tinidazole concentration in the tissue, wherein the tissue is mounted on polycarbonate membranes having 0.4 µm pores, wherein the culture medium/receiver fluid is VEC-100-ASY available from MatTek Corporation (Ashland, Mass.).

In particular embodiments, the mean peak concentration can range from about 1500 ng tinidazole/mg tissue to about 4500 ng tinidazole/mg tissue. In other embodiments, the mean peak concentration can range from about 1800 to about 4200 ng tinidazole/mg tissue. In still further embodiments, the mean peak concentration can range from about 2000 ng tinidazole/mg tissue to about 4000 ng tinidazole/mg tissue. In certain embodiments, the mean peak concentration can be about 2000 ng tinidazole/mg tissue, about 2700 ng tinidazole/mg tissue, or about 3400 ng tinidazole/mg tissue.

In other embodiments, the mean peak concentration can range from 1500 ng tinidazole/mg tissue to 4500 ng tinidazole/mg tissue. In other embodiments, the mean peak concentration can range from 1800 to 4200 ng tinidazole/mg tissue. In still further embodiments, the mean peak concentration can range from 2000 ng tinidazole/mg tissue to 4000 ng tinidazole/mg tissue. In certain embodiments, the mean peak concentration can be 2000 ng tinidazole/mg tissue, 2700 ng tinidazole/mg tissue, or 3400 ng tinidazole/mg tissue.

In a further embodiment, the formulation can have a mean peak tinidazole concentration that satisfies the formula:

$$y = 2834x - 804.83$$

over a range of tinidazole concentrations of from about 0.8% (w/w) to about 1.8% (w/w), wherein y is the mean peak concentration of tinidazole measured in the culture and x is the concentration of tinidazole in the formulation.

EXAMPLES

The formulations and methods are now further detailed with reference to the following examples. These examples are provided for the purpose of illustration only and the formulations and methods described herein should in no way be construed as being limited to these examples. Rather, the formulations should be construed to encompass any and all variations which become evident as a result of the teaching provided herein.

The 60% IPA solution (w/w) described below was prepared by adding 600 g of IPA USP and 400 g of water USP to a 1.0 L vessel and mixing the combined solution well.

The 0.05 M citric acid buffer solution used and described in the examples below was prepared as follows. 21.016 g of citric acid monohydrate was added to a 2.0 L vessel with 2000 mL of water ("solution 1"). In a separate 2 L vessel, 25.806 g of sodium citrate (anhydrous) was mixed with 2000 mL of water until the material was dissolved ("solution 2"). Finally, 550 mL of solution 1 and 450 mL of solution 2 were combined and mixed in an appropriately sized vessel. The pH of the resulting solution was measured at 3.30 using a standard pH electrode.

Example 1

Timidazole Gel Formulations

Formulations having 1%, 1.25%, and 1.5% tinidazole as shown in Table 1, below, were prepared according to the following general procedure.

An appropriate quantity of poloxamer 407 and citrate buffer were combined in an appropriate vessel to give a suspension. The vessel was then placed in an ice-water bath and the suspension was mixed at 400 rpm for 6 hours to dissolve all of the poloxamer. Upon complete dissolution, the clear solution was warmed to room temperature (22° C.) and this temperature was maintained with a water bath.

Next, the appropriate quantities of 60% IPA, benzyl alcohol, DMI and tinidazole were combined in an appropriately sized vessel. The resulting mixture was then heated at 37° C. for approximately 30 minutes until all of the tinidazole was dissolved. Once dissolved, the solution was then cooled to room temperature and added slowly and with agitation to the poloxamer solution. The resulting mixture was then stirred at low RPM until uniform. After stirring, the mixing apparatus was removed and the resulting material was allowed to settle for 24 hours to allow trapped air to bubble to the surface.

TABLE 1

| Formulation # | Poloxamer 407 (g)/(% w/w) | Citrate Buffer (g)/(% w/w) | Benzyl Alcohol (g)/(% w/w) | 60% IPA (g)/(% w/w) | DMI (g)/(% w/w) | Tinidazole (g)/(% w/w) |
|---|---|---|---|---|---|---|
| F1 | 10.00 (20.00) | 24.79 (49.58) | 1.56 (3.12) | 6.00 (12.00) | 6.90 (13.80) | 0.750 (1.50) |
| F2 | 9.50 (19.00) | 26.62 (53.24) | 1.43 (2.86) | 5.50 (11.00) | 6.33 (12.6) | 0.625 (1.25) |
| F3 | 9.00 (18.00) | 28.50 (57.00) | 1.25 (2.50) | 5.00 (10.00) | 5.75 (11.50) | 0.500 (1.00) |

Example 2

Formulations 4 and 5, described in Table 2, below, were prepared according to the following general procedure.

An appropriate quantity of poloxamer 407 and citrate buffer were combined in an appropriate vessel to give a suspension. The vessel was then sealed and placed on a shaker rotating at ~160 rpm in a cold room at 4° C. and was left shaking overnight until complete dissolution of the poloxamer was observed. The resulting clear solution was allowed to stand at 4° C. for a few hours to remove air bubbles present in the solution. The poloxamer solution was then placed in an incubator at 18° C. for approximately 30 min.

Next, the appropriate quantities of DMI, 70% IPA, benzyl alcohol, and tinidazole were combined in an appropriately sized vessel. The resulting mixture was heated at 37° C. for approximately 10 min until complete dissolution of the tinidazole was observed. The clear solution was then cooled to room temperature (22° C.) and was added slowly with agitation (shaking) to the poloxamer solution at room temperature (22° C.) until a uniform clear solution was obtained. The final formulations were allowed to stand at room temperature (22° C.) to remove air bubbles.

TABLE 2

| Formulation # | 26% Poloxamer Gel Soln (g) | DMI (ml) | 70% IPA (ml) | Benzyl Alcohol (ml) | Citrate Buffer (ml) | Tinidazole (mg) | Tinidazole % |
|---|---|---|---|---|---|---|---|
| F4 | 14.23 | 2.2 | 2.4 | 0.55 | 0.37 | 250 | 1.25 |
| F5 | 14.23 | 2.0 | 2.2 | 0.50 | 0.87 | 200 | 1.00 |

The cold temperature stability of formulations 4 and 5 was tested by cooling the formulations to a specified temperature for 24 hours and then warming the formulations to room temperature (22° C.) where they were allowed to stand for a further 24 hours. During the temperature challenge, the formulations were visually evaluated for the formation of crystals either at low temperature or upon subsequent warming. The results are shown in Table 3.

TABLE 3

|  | Temp (° C.) | | | |
| --- | --- | --- | --- | --- |
| Formulation # | 18 | 14 | 10 | 6 |
| F4 | No crystals | No crystals | Crystals | Crystals |
| F5 | No crystals | No crystals | No crystals | No crystals |

This data demonstrates that the formulations can be subjected to relatively cool temperatures and maintain tinidazole in solution, even at high tinidazole concentrations.

Example 3

In Vitro Drug Release

To determine whether tinidazole would be released upon intravaginal administration, an in vitro test (membrane-free model) simulating formulation erosion in the vaginal cavity was conducted. Two different tinidazole 1.25% gel formulations were prepared (F6=18.6% gel, 1.75% hydroxypropyl methylcellulose (HPMC), Tmelt=31° C.; F7=19.01% gel, no HPMC, Tm=29° C.). Specifically, 1 g of each formulation was added to a pre-weighed vial equilibrated at 37° C. Next, 0.5 ml of deionized water was slowly added to the top of the vial and the vial was allowed to stand for 2 hours, 6 hours, 24 hours, or 4 days. After the appropriate amount of time passed, the liquid supernatant sitting on top of the formulation was carefully removed, weighed, and analyzed for its tinidazole concentration using standard HPLC methodology. All studies were conducted in triplicate to ensure quality data. This membrane-free system is a suitable choice to mimic natural gel erosion in the vaginal cavity.

These studies showed that the formulations described herein are susceptible to gradual erosion/dissolution with minimal or no agitation.

Example 4

Vaginal Irritation in Rabbits

Formulations F1, F2, and F3 (1 mL) (as described in Example 1) and Vehicle Formulations V1, V2, and V3 (as described below in Table 4) were each administered into the vaginal vaults of 3 female test rabbits (New Zealand White strain) for five consecutive days. The formulations were administered with a blunt tipped animal-feeding needle attached to a 3 cc syringe. Control animals were dosed with 1 mL of a 0.9% saline solution under identical conditions.

TABLE 4

| Vehicle Formulations | | | | | | |
| --- | --- | --- | --- | --- | --- | --- |
|  | Poloxamer (g)/ (% w/w) | Citrate Buffer (g)/(% w/w) | Benzyl Alcohol (g)/(% w/w) | 60% IPA (g)/ (% w/w) | DMI (g)/ (% w/w) | Tinidazole (g)/(% w/w) |
| V1 | 10.00 (20.00) | 40.00 (80.00) | N/A | N/A | N/A | N/A |
| V2 | 10.00 (20.00) | 25.54 (51.10) | 1.56 (3.12) | 6.00 (12.00) | 6.90 (13.80) | N/A |
| V3 | 8.75 (17.50) | 30.45 (60.90) | 1.13 (2.26) | 4.50 (9.00) | 5.18 (10.36) | N/A |

Prior to the first dose of the control, vehicle, or active formulations, and before each daily dose thereafter, the external vaginal tissues of each animal was observed for erythema, exudate, and edema according to the scoring system shown in FIG. 1. The results of the daily monitoring of the external vaginal tissue are shown in FIGS. 2 (V1), 3 (V2), 4 (V3), 5 (Formulation 1), 6 (Formulation 2), and 7 (Formulation 3). As can be seen in the Figures, each of the formulations caused minimal or no visual changes in the external vaginal tissue of the subject animals.

Following completion of the protocol, the animals were sacrificed with sodium pentobarbital and the vaginal tissue of each animal was carefully removed. The tissue was then observed macroscopically and scored for irritation and injury to the epithelial layer. Following macroscopic observation, the tissue was sectioned to provide the cervical, central, and caudal portions. The samples were then individually placed in 10% neutral buffered formalin and submitted for histopathological evaluation. Samples were evaluated based on the criteria shown in FIG. 8.

Specific results, corresponding to formulations V1, V2, V3, F1, F2, and F3 are shown in FIGS. 9A and 9B through FIGS. 14A and 14B, respectively. Overall, each of the vehicle and drug-containing formulations showed minimal observable effects, suggesting that the formulations are suitable for intravaginal administration despite the propensity for the individual components of the formulations to cause irritation.

Example 5

Isolation and Identification of Bacterial Strains Associated with Bacterial Vaginosis To obtain clinical isolates from women suspected of having bacterial vaginosis, 192 microscope slides from 192 vaginal swabs (obtained from women consulting in the Quebec City area) submitted for Nugent scoring were analyzed. Based on microscopic observations of bacterial cell morphology and Nugent score, 46 swabs were selected for bacterial isolation.

Bacterial isolates were identified by polymerase chain reaction (PCR) and DNA sequencing of the 16S rRNA gene. A total of 30 swabs were positive for at least one isolate of *Bacteroides* spp., *Gardnerella vaginalis*, *Peptostreptococcus* spp., *Prevotella* spp., *Lactobacillus* spp., or *Mobiluncus* spp. Isolates from all bacterial strains of interest were identified, resulting in 39 strains in total. Isolates were frozen and stored for later use.

Example 6

Antimicrobial Susceptibility Testing

Reference type strains (8 strains total) were thawed and tested against the formulations described herein. After initial culture of the selected frozen preserved bacteria from Example 5, and 2 additional passages (sub-cultures)—(total=3 passages) on blood agar and colony suspension in saline, the saline suspension was used to inoculate the surface of *Brucella* Agar with 5% Sheep Blood. Small (6 mm) discs with 10 µL of formulations F1, F2, or F3 and control gel formulation were centered on the agar plates and incubated at 35° C. under anaerobic conditions. The diameter of the inhibition zone in mm was measured after 48 to 96 hours of incubation, depending on bacterial strains. Testing was conducted in triplicate.

Testing showed that a specific *Lactobacillus jensenii* strain and *Mobiluncus curtisii* subsp. *Holmesii* strain were not affected by the presence of formulations F1, F2, and F3. But *B. fragilis, G. vaginalis, L. crispatus, M. mulieris, P. anaerobius*, and *P. bivia* were each inhibited by the formulations described herein, with inhibition zones varying from about 20 to about 60 mm. No inhibition was observed using control formulations F1, F2, and F3 prepared without tinidazole.

Example 7

MIC Determination

Minimum inhibitory concentrations were determined for 39 clinical isolates and 8 reference strains as described below.

A hemin stock solution (5 mg/mL) was prepared by dissolving 0.1 g of hemin in 2 mL of 1.0 N NaOH. Next, the volume was adjusted to 20 mL with distilled water and the mixture was sterilized at 121° C. for 15 minutes.

A stock vitamin K solution (10 mg/mL) was prepared by combining 0.2 mL of vitamin $K_1$ with 20 ml of 95% ethanol. A working solution (1 mg/ml) was prepared by combining 1 ml of the stock vitamin K solution with 9 ml sterile deionized water.

Laked sheep blood was prepared by freezing defibrinated sheep blood at −80° C. The blood was then thawed slowly at 2 to 8° C. overnight. The thawed blood was mixed thoroughly before use and warmed in a 48 to 50° C. water bath immediately before adding to a molten *brucella* agar base.

Serial dilutions of formulations F1 (1.5% tinidazole), F2 (1.25% tinidazole), and F3 (1.0% tinidazole) were prepared at the following concentrations—F3: 1,000 μg/ml; 500 μg/ml; 250 μg/ml; 125 μg/ml; 62.5 μg/ml; 31.25 μg/ml; and 15.63 μg/ml; F2: 1,250 μg/ml; 625 μg/ml; 312.5 μg/ml; 156.25 μg/ml; 78.125 μg/ml; 39.06 μg/ml; and 19.53 μg/ml; F1: 1,500 μg/ml; 750 μg/ml; 375 μg/ml; 187.5 μg/ml; 93.75 μg/ml; 46.875 μg/ml; 23.44 μg/ml; and 11.72 μg/ml.

*Brucella* laked blood agar with vitamin $K_1$ and hemin was prepared as follows. 28 g of *brucella* broth powder was combined with 15 g of agar and 1 ml each of the hemin stock solution and vitamin K working solution in 1 L distilled water. The solution was boiled to dissolve the agar and subsequently autoclaved at 121° C. for 15 minutes. The resulting agar solution was then cooled to about 50° C. and 50 ml of sterile laked sheep blood was added. Next, 2 ml of each of a given serial dilution of formulation F1, F2, or F3 (as described above) was combined with 18 ml of the laked sheep blood containing agar solution. The resulting solution was then added to a 15×100 mm Petri dish and allowed to solidify and prereduce in an anaerobic chamber for at least 24 hours. This gave tinidazole infused agar plates having tinidazole concentrations of 100 μg/ml, 50 μg/ml, 25 μg/ml, 12.5 μg/ml, 6.25 μg/ml, 3.125 μg/ml, and 1.563 μg/ml (F3); 125 μg/ml, 62.5 μg/ml, 31.25 μg/ml, 15.63 μg/ml, 7.81 μg/ml, 3.91 μg/ml, and 1.95 μg/ml (F2); and 150 μg/ml, 75 μg/ml, 37.5 μg/ml, 18.75 μg/ml, 9.37 μg/ml, 4.69 μg/ml, and 2.34 μg/ml (F1).

As in Example 6, cultures of the frozen preserved bacteria from Example 5, were grown on blood agar for 24 to 96 hours. Colonies of similar morphology were selected and suspended in prereduced *brucella* broth to achieve a turbidity equivalent to 0.5 McFarland.

The resulting suspension was then used to inoculate the tinidazole infused and control agar plates in triplicate. MIC was determined by comparing control plates (not infused with tinidazole) against each of the inoculated tinidazole-infused plates. MIC was read as the minimum concentration at which a marked reduction in bacterial growth was observed. The data is reported in Table 5.

TABLE 5

| Bacteria | MIC (μg/ml) |
|---|---|
| *Bacteroides fragilis* | Less than about 5, and in certain instances, less than about 1.6 |
| *Gardnerella vaginalis* | From less than about 2 to about 150; about 2 to about 125; or about 2 to about 100 |
| *Lactobacillus crispatus* | Less than about 50, and in certain instances, less than about 30, or less than about 25 (reference strain) |
| *Mobiluncus mulieris* | From about 15 to about 25 |
| *Peptostreptococcus anaerobius*, *Prevotella bivia*, *Prevotella disiens*, and *Prevotella timonensis* | Less than about 2 |

The MICs for each identified strain of *Lactobacillus gasseri, Lactobacillus iners, Lactobacillus jensenii, Lactobacillus vaginalis*, and *Mobiluncus curtisii* were each greater than 150 μg/ml. The non-reference strain of *Lactobacillus* crispatus was similarly unaffected by tinidazole at the highest concentration tested. This data demonstrates that these strains, and in particular the *lactobacillus* strains which are important for vaginal health, are not inhibited by tinidazole at concentrations sufficient to inhibit bacterial strains associated with bacterial vaginosis.

In addition to testing the formulations including tinidazole as noted above, formulations equivalent to formulations F1, F2, and F3 were prepared without tinidazole to determine the anti-microbial activity attributable to the components of the F1, F2, and F3 formulations. These tinidazole-free formulations were appropriately diluted and tested against the various identified bacterial strains. No inhibition of growth for any bacterial isolate was observed using the tinidazole free formulations.

Example 8

Franz Cell Diffusion Testing

Formulations F1, F2, and F3 were subjected to Franz cell diffusion testing. In the Franz cell (PermeGear, Inc. Hellertown, Pa.), a 0.40 μm pore polycarbonate membrane (Fisher Scientific, Pittsburgh, Pa.) was used. The membrane area was 1.77 $cm^2$. A 480 μL sample of each test formulation was loaded in the donor cell. The receptor cell contained 8 mL of 0.05 M citrate buffer, pH 3.3 ("receiver fluid"). At 0.5, 1, 2, 3, 4, and 6 hours (n=6 replicates), a 500 μl sample was removed from the receptor cell and replaced with 500 μL of fresh buffer. The study was conducted at 37° C. Concentration of tinidazole in the receiver fluid removed from the Franz cell was determined by LC-MS/MS.

Drug concentration per unit membrane area was plotted against the square root of time in hours. FIG. 15 shows the mean±standard deviation of tinidazole released (μmol)/cm$^2$ versus square root of time in hours.

There was no gel left in any of the chambers at the end of 6 hours. Due to tinidazole saturation in the receiver chambers occurring around 180 minutes, all in vitro release rates (slopes) were calculated using only the linear portion of the curve ($R^2 \geq 0.9$, i.e., samples up to and including 180 minutes). Rate and recovery data are shown in Table 6, below.

TABLE 6

| Formulation | Rate[a] ([μmol/cm$^2$/√t(h)]) | % Recovery[a] (at 6 hours) |
|---|---|---|
| F3 | 6.04 ± 0.893 | 98.5 ± 5.34 |
| F2 | 7.56 ± 1.32 | 96.5 ± 4.24 |
| F1 | 8.70 ± 0.964 | 89.6 ± 4.51 |

[a] = Mean ± Standard Deviation

As can be seen in Table 6, release rate increased as tinidazole concentration increased. Based on 90% confidence intervals computed for the ratios of the median in vitro release rate for pairs of formulations F1, F2, and F3 (e.g. F1 and F2; F1 and F3; F2 and F3), the F1 and F2 comparison showed these formulations can be considered to have equivalent release rates (default "no difference" 90% confidence intervals limits were 75% to 133.33%). The statistical equivalence of release rates of the F2 and F3 formulations was not determined by the present comparison, while the difference in release rate between F1 and F3 was statistically significant.

Example 9

Flux and Tissue Association Using EpiVaginal™ Tissue

EpiVaginal™ tissue (produced from normal human-derived vaginal-ectocervical epithelial cells) full thickness tissues (VEC-100-FT) on polycarbonate membranes (NUNC® single well tissue culture plate, pore size 0.4 μm) and culture medium (VEC-100-ASY) were purchased from MatTek Corporation (Ashland, Mass.).

The culture medium (VEC-100-ASY) was pre-warmed at 37° C. Under sterile conditions and using sterile forceps, the EpiVaginal™ tissues were transferred into 12-well plates containing the pre-warmed culture medium. Then, the 12-well plates containing the EpiVaginal™ tissue samples were placed in a humidified incubator (37±2° C., 5±1% $CO_2$) for overnight recovery. The next morning, the culture medium in the plates was aspirated, and the EpiVaginal™ tissues were transferred into new 24-well plates.

Figure 16:
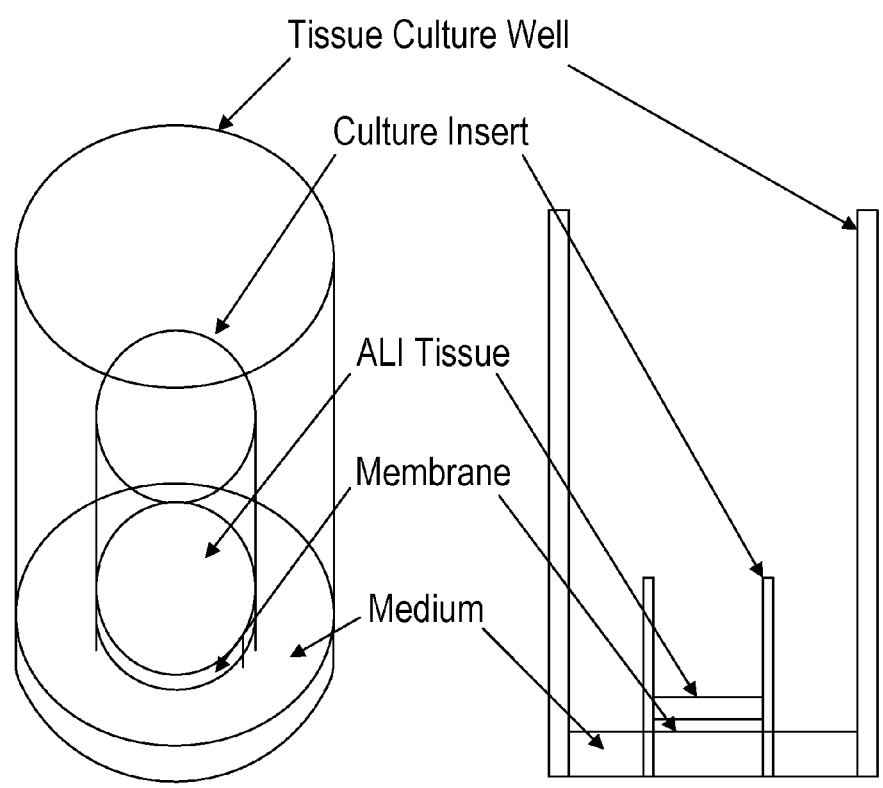
FIG. 16 is a graphical representation of a culture well and insert used in the EpiVaginal™ tissue studies described herein.
Figure 17:
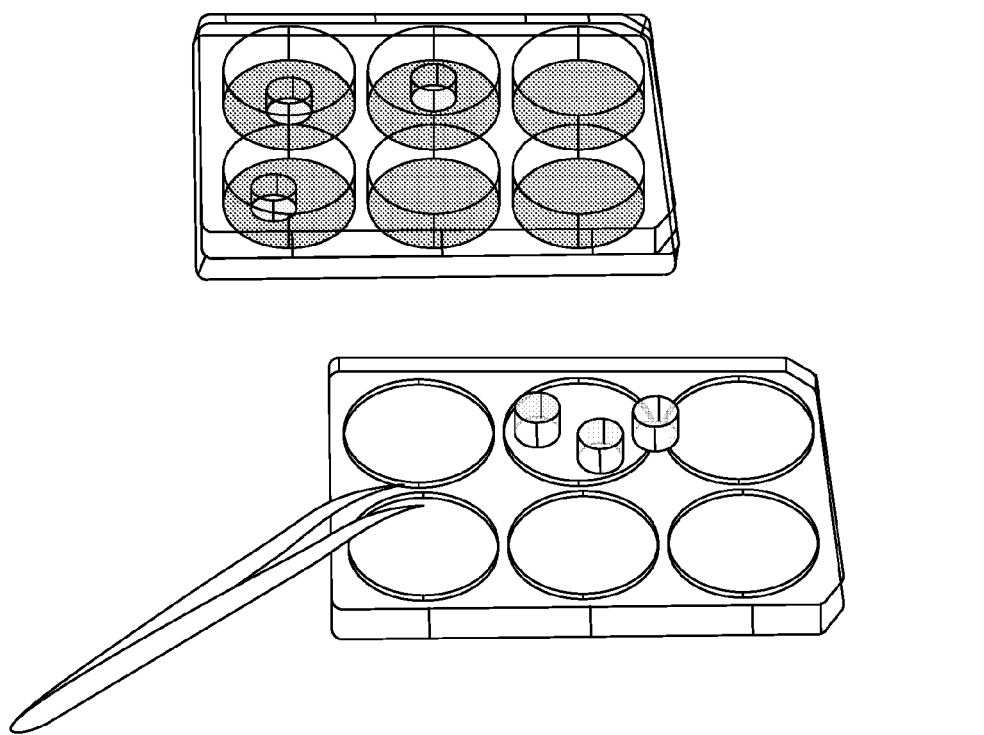
FIG. 17 is an example of a multi-well culture plate representative of the types of multi-well culture plates that can be used in the EpiVaginal™ tissue studies described herein.

An aliquot (100 μL) of one of formulation F1, F2, or F3 was added to the apical (AP) side of EpiVaginal™ tissue in the culture insert (see FIG. 16), and 500 μL, of the culture medium was added to the basolateral (BL) side of the insert. For a control group, an aliquot (100 μL) of culture medium was added to the AP side of the insert, and 500 μL, of culture medium was added to the BL side (the "Mediuim" in FIG. 16). All dosing was performed under sterile conditions in a laminar flow hood.

The plates containing the tissue were incubated in a humidified incubator (37±1° C., 5±1% $CO_2$) during the study and removed only for assays at 1, 2, 4, 6, 8, 24, or 48 hours. Four replicates were studied at each time point, for a total of 28 samples per formulation. The noted studies were run in parallel such that plates assayed at a given time point were not assayed at any other time point.

At the completion of each incubation time point, the 500 μL of culture medium on the BL side was analyzed for tinidazole content using LC-MS/MS. The tinidazole concentrations recorded at the 1, 2, and 4 hour time points were used to calculate the mean flux rate in EpiVaginal™ tissue culture.

Simultaneously, the EpiVaginal™ tissue culture was removed from the reactor and the contents in both the AP and BL sides were carefully aspirated and the tissues were washed twice with assay media (300 μL) to remove residual formulations. The rinses were discarded and the tissue was gently blotted on a Kim wipe and weighed. The tissues were stored at −80° C. until further analysis, which comprised homogenization with the resulting tissue lysates analyzed by LC-MS/MS to determine the tissue tinidazole concentration at each time point.

TABLE 7

| Formulation | Mean Flux Rate (nmol/cm$^2$/min) | Mean Peak Tinidazole Concentration in EpiVaginal ™ Tissue at 1 Hour (ng/mg)[b] | Mean[a] Tinidazole Receiver Fluid Concentration (nM) | | |
|---|---|---|---|---|---|
| | | | 1-Hour | 2-Hour | 4-Hour |
| F3 | 18 ± 0.993 | 2,017 ± 161 | 1,144,500 ± 149,089 | 2,290,000 ± 303,425 | 4,400,000 ± 199,499 |
| F2 | 22.5 ± 2.31 | 2,762 ± 533 | 1,517,500 ± 207,746 | 2,855,000 ± 245,289 | 5,567,500 ± 279,687 |
| F1 | 19.0 ± 3.52 | 3,434 ± 498 | 1,735,000 ± 270,000 | 2,627,500 ± 257,472 | 5,105,000 ± 713,559 |

[a] n = 4 replicates per treatment at 1-, 2-, and 4-hour time point.

[b] Mean peak EpiVaginal ™ tissue concentrations occurred at the 1-hour time point for all treatments (4 replicates).

As can be seen in Table 7, the mean tinidazole tissue flux rates differed by less than 20% between formulations F1, F2, and F3, implying that flux rates were not concentration dependent. Even though flux rates were not concentration dependent, concentration-dependent increases in the mean maximal EpiVaginal™ tissue-associated tinidazole concentrations were observed at the 1 hour incubation time point. All of the maximal tissue-associated tinidazole concentrations exceeded 2,000 ng/mg of tissue across the 3 formulations evaluated. Additionally, for each of formulations F1, F2, and F3, the receiver fluid mean tinidazole concentrations increased approximately proportionally with incubation times of up to 4 hours duration.

It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A formulation suitable for the intravaginal delivery of tinidazole to a subject in need thereof, the formulation comprising about 20% poloxamer 407 (w/w), about 49.6% citrate buffer (w/w), about 3.1% benzyl alcohol (w/w), about 12% (w/w) of a 60% (w/w) solution of isopropanol in water, about 13.8% dimethylisosorbide (w/w), and about 1.5% tinidazole (w/w).

2. A formulation suitable for the intravaginal delivery of tinidazole to a subject in need thereof, the formulation comprising about 19% poloxamer 407 (w/w), about 53% citrate buffer (w/w), about 2.9% benzyl alcohol (w/w), about 11% (w/w) of a 60% (w/w) solution of isopropanol in water, about 12.7% dimethylisosorbide (w/w), and about 1.25% tinidazole (w/w).

3. A formulation suitable for the intravaginal delivery of tinidazole to a subject in need thereof, the formulation comprising about 18% poloxamer 407 (w/w), about 57% citrate buffer (w/w), about 2.5% benzyl alcohol (w/w), about 10% of a 60% (w/w) solution of isopropanol in water, about 11.5% dimethylisosorbide (w/w), and about 1% tinidazole (w/w).

* * * * *